(12) United States Patent
Girgis

(10) Patent No.: US 7,153,260 B1
(45) Date of Patent: Dec. 26, 2006

(54) LARYNGOSCOPE FOR SIMULTANEOUSLY FACILITATING THE ILLUMINATING OF A THROAT PATHWAY AND INSERTING AN INTUBATION TUBE

(76) Inventor: Magdy S Girgis, 660 E. 98th St., Apt. 3-G, Brooklyn, NY (US) 11236

( * ) Notice: Subject to any disclaimer, the term of this patent is extended or adjusted under 35 U.S.C. 154(b) by 409 days.

(21) Appl. No.: 10/790,554

(22) Filed: Mar. 1, 2004

(51) Int. Cl.
*A61B 1/267* (2006.01)

(52) U.S. Cl. ................. 600/196; 600/193; 600/194; 600/199

(58) Field of Classification Search ............ 600/185, 600/193, 194, 196, 199
See application file for complete search history.

(56) References Cited

U.S. PATENT DOCUMENTS

| | | | |
|---|---|---|---|
| 1,067,788 A * | 7/1913 | Atkinson | 111/16 |
| 1,568,732 A * | 1/1926 | Haslinger | 600/196 |
| 3,943,920 A | 3/1976 | Kandel | |
| 4,114,609 A | 9/1978 | Moses | |
| 4,573,451 A | 3/1986 | Bauman | |
| 4,592,343 A | 6/1986 | Upsher | |
| 5,003,962 A | 4/1991 | Choi | |
| 5,498,231 A * | 3/1996 | Franicevic | 600/190 |
| 5,938,591 A * | 8/1999 | Minson | 600/191 |
| 6,095,972 A * | 8/2000 | Sakamoto | 600/190 |
| 6,251,069 B1 | 6/2001 | Mentzelopoulos et al. | |
| 2002/0165433 A1* | 11/2002 | Stihl | 600/196 |
| 2005/0234303 A1* | 10/2005 | McMorrow | 600/189 |

* cited by examiner

*Primary Examiner*—John P. Leubecker
(74) *Attorney, Agent, or Firm*—Richard L. Miller

(57) ABSTRACT

An improved laryngoscope of the type having a stationary handle, a stationary blade affixed to the stationary handle, a tip pivotally attached to the stationary blade, a movable handle pivotally attached to the stationary blade, and an arm pivoting the tip downwardly when the movable handle is moved towards the stationary handle depressing the epiglottis. The improvement includes a movable blade pivotally attached to the stationary blade and affixed to the movable handle so as to allow the movable blade to pivot away from the stationary blade when the movable handle is moved towards the stationary handle and spread the posterior tissue defining the superior opening of the larynx away from the epiglottis simultaneously as the tip depresses the epiglottis and both thereby opening up the trachea exposing the larynx, and a lock locking the movable blade in a desired positioned by locking the movable handle affixed thereto.

16 Claims, 4 Drawing Sheets

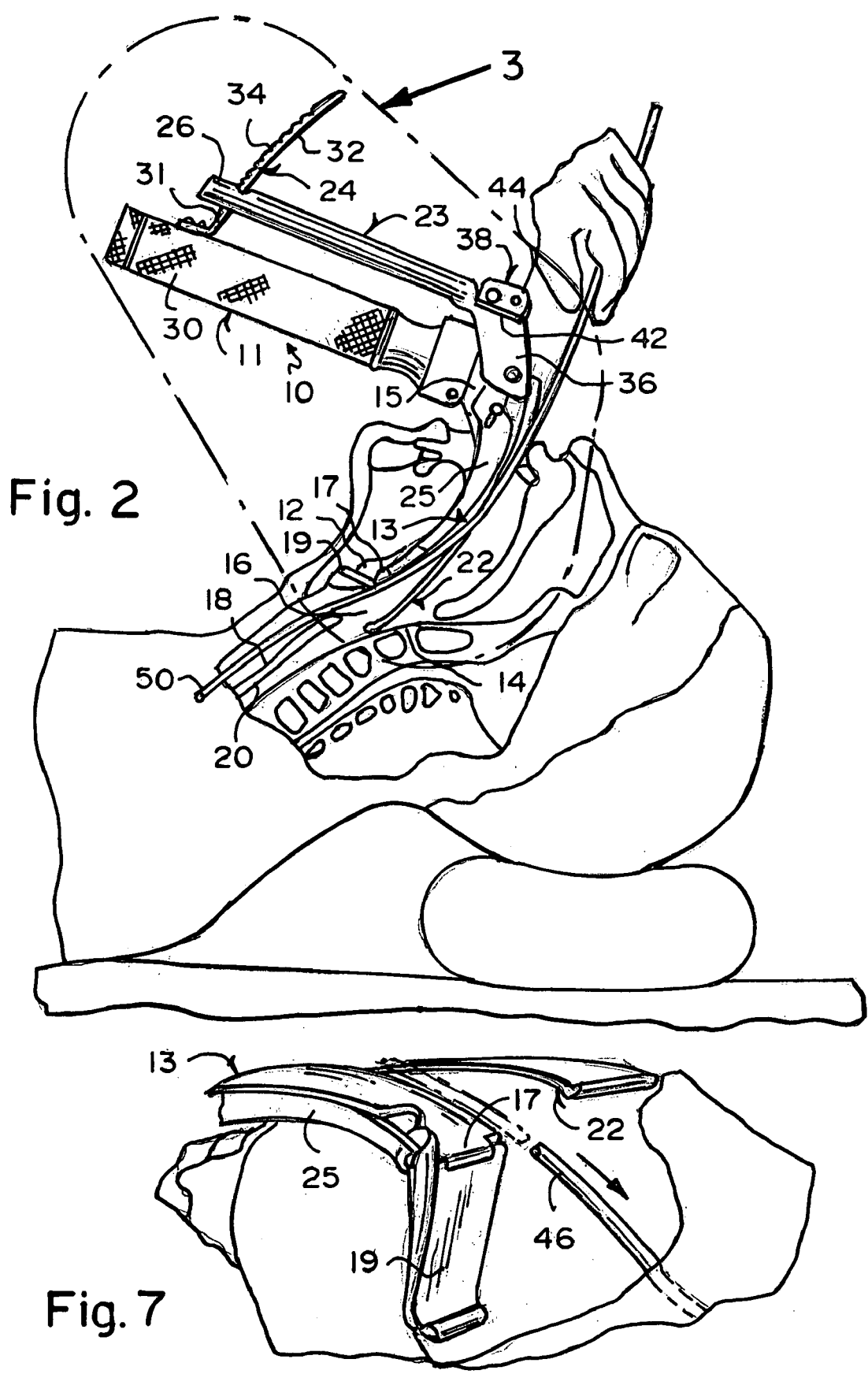

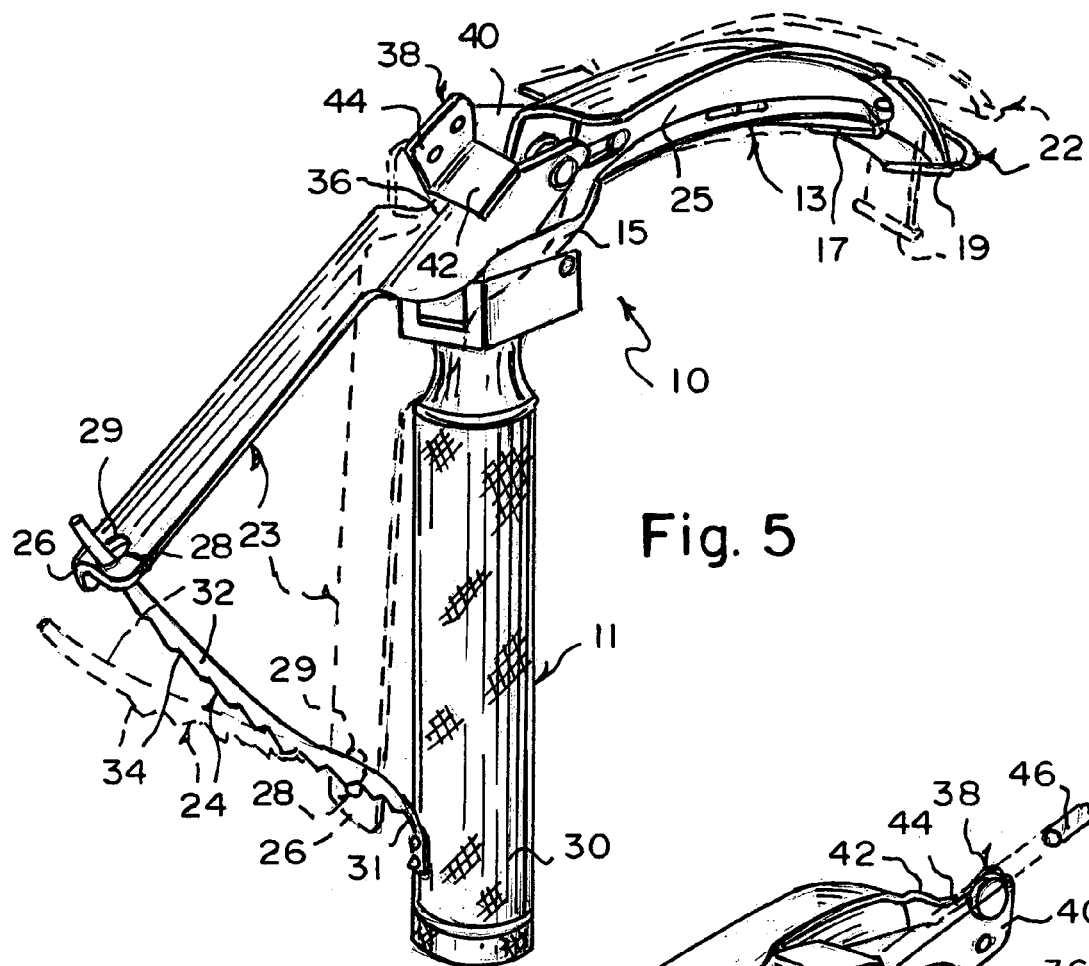
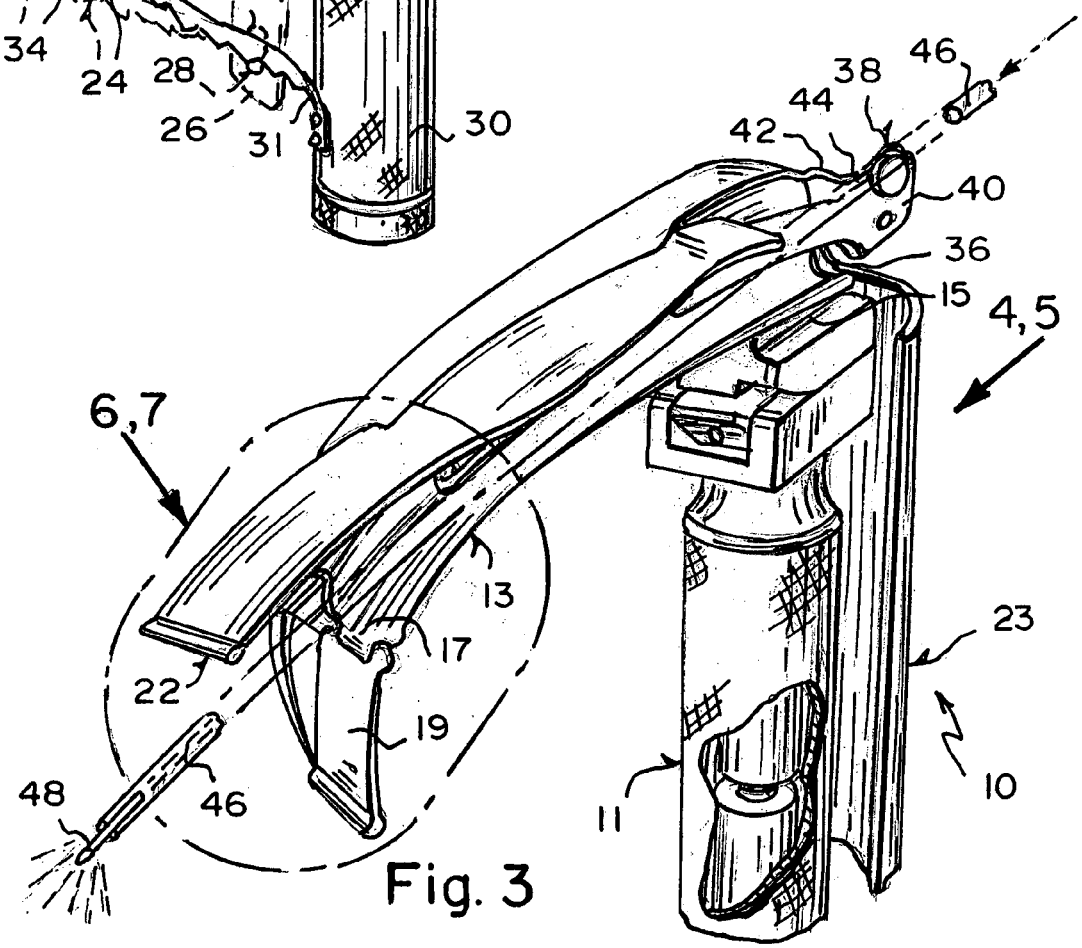
Fig. 5
Fig. 3

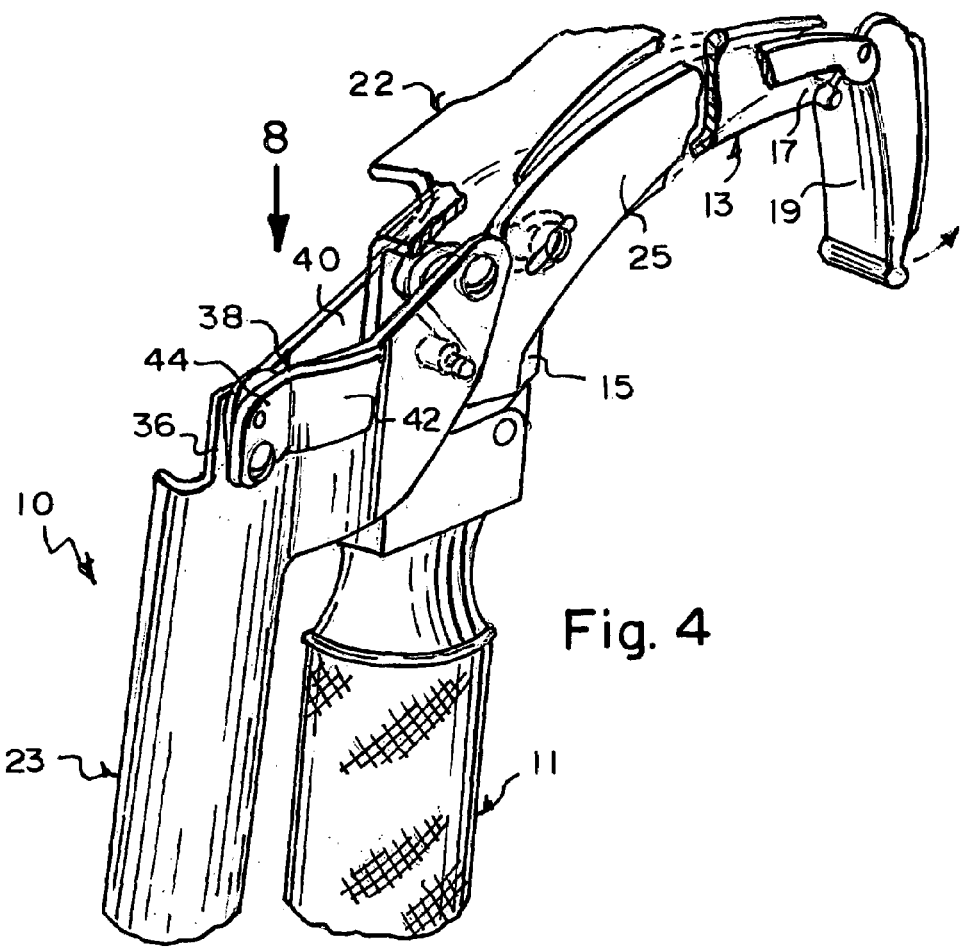
Fig. 4
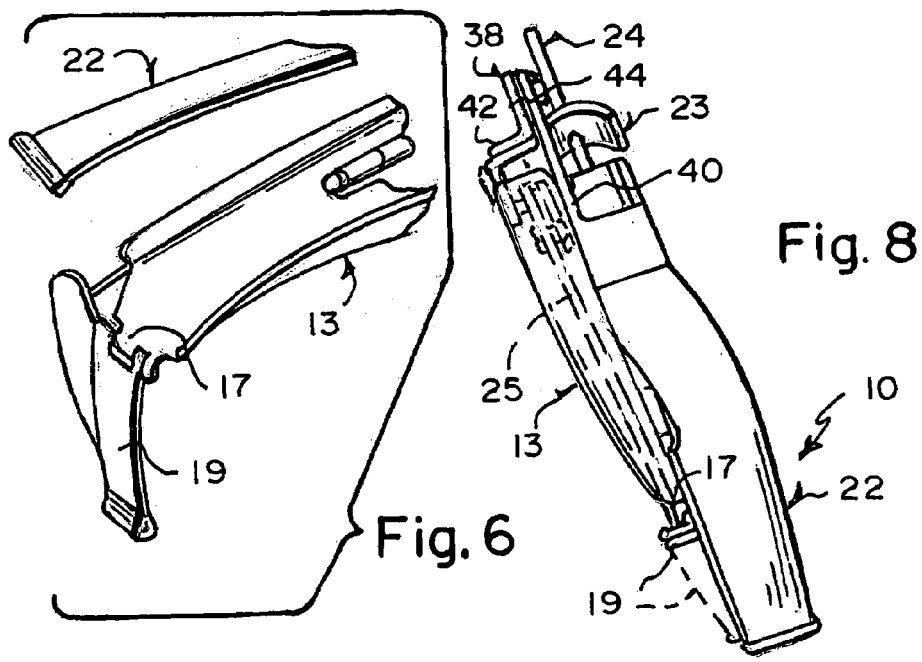
Fig. 6
Fig. 8

LARYNGOSCOPE FOR SIMULTANEOUSLY FACILITATING THE ILLUMINATING OF A THROAT PATHWAY AND INSERTING AN INTUBATION TUBE

BACKGROUND OF THE INVENTION

1. Field of the Invention

The present invention relates to a laryngoscope. More particularly, the present invention relates to a laryngoscope for simultaneously spreading the epiglottis and the posterior tissue defining the superior opening of the larynx away from each other for opening up the trachea and exposing the larynx.

2. Description of the Prior Art

Laryngoscopes generally comprise a blade and a cooperating, detachable handle which are connected together into an L-shaped configuration. When using the device to view the larynx, the surface on the blade adjacent the handle is used to press against the tongue and mandible of a patient in a supine position in order to prevent the patient's tongue from obstructing the view during the visual examination. While the instrument is useful in examining the larynx, the primary function of the laryngoscope is to expose the larynx in order to facilitate the insertion of an endotracheal tube into the trachea of the lungs to administer gases.

During the use of the instrument, when pressed against the patient's tongue and mandible, the tip or distal end of the blade is usually positioned at the Junction between the base of the tongue and the base of the epiglottis which is thin, leaf shaped lamella in front of the superior opening of the larynx. With most patients, the epiglottis will be lifted sufficiently to expose the larynx by rotating the instrument anteriorly (i.e., longitudinally). Usually the patient's head is tilted backwardly to facilitate the examination.

With a small fraction of patients, the epiglottis will not be lifted sufficiently to expose the larynx in the usual laryngoscopic procedures. Unfortunately, the small percentage of patients having the anatomical structure which makes the examination of the larynx difficult cannot be determined by visually examining the epiglottis before inserting the laryngoscope. Usually, it is not until the anesthesiologist tries to expose the larynx to administer anesthetic gases, that the difficulty is encountered. The anesthesiologist must then replace the blade being used with a longer and straighter blade which is used to contact the upper edge of the epiglottis and push the epiglottis anteriorly to expose the larynx. However, the view of the larynx is not very complete in this instance and damage is frequently done to the tissue trying to push the epiglottis far enough out of the way to effectively expose the larynx.

The need for a laryngoscope which will readily expose the larynx in those patients in which the normal laryngoscopic procedures do not work has been long felt. The present invention satisfies these needs.

This need has been forfilled by U.S. Pat. No. 4,573,451 to Bauman, which is incorporated herein by reference thereto, and which forms the basis for the improvements taught by the present invention.

Generally Bauman teaches a laryngoscope blade which has a tip at the distal end thereof which is capable of being bent or flexed in the direction of the handle of the laryngoscope. Operable means are provided, preferably at the proximal end of the blade, to bend or flex the tip. When the blade is inserted into a patient's throat so that the bendable tip is located at the base of the patient's epiglottis, the operable means of the bendable tip can be actuated so the tip will bend and thereby further lift the patient's epiglottis in order to expose the patient's larynx. The laryngoscope blade is particularly suitable to the few patients in which the usual laryngoscopic procedures do not adequately expose the patient's larynx.

Typically, as shown in FIG. 1, the laryngoscope 10 has a stationary handle 11, a stationary blade 13 having a proximal end 15 from which it extends generally normally forwardly from the stationary handle 11 and a distal end 17, a tip 19 pivotally attached to the distal end 17 of the stationary blade 13, a movable handle 23 pivotally attached to the proximal end 15 of the stationary blade 13 and operatively connected to the tip 19, and an arm 25 operatively attached to the movable handle 23 and the tip 19 and pivoting the tip 19 downwardly when the movable handle 23 is moved towards the stationary handle 11 for depressing the epiglottis. In contradistinction, as best seen in FIGS. 2 and 3, the flexible tip laryngoscope 10 of the present invention has a double set of blades wherein the addition of a movable blade 22 is for clearing a path for a fiber optic seeing stylet 46 and simultaneously lifting patient's epiglottis 12 while pushing the tongue and the posterior pharyngeal wall out of the way so as to permit light from the light tip element 48 of to illuminate the path way and facilitate the inserting of intubation tube 50.

Numerous other innovations for laryngoscopes have been provided in the prior art that will be described. Even though these innovations may be suitable for the specific individual purposes to which they address, however, they differ from the present invention.

A SECOND EXAMPLE, U.S. Pat. No. 3,943,920 to Kandel teaches a laryngoscope blade that includes an upper wall, a lower wall, and a side wall joining the upper and lower walls. The upper wall includes an upper lip engaging portion and an upper gum engaging portion which are contiguous with one another. The lower wall includes a tongue engaging portion and a tip portion disposed for engaging and lifting the epiglottis. The gum portion is substantially parallel to a major extent of the lower wall, whereas the lip portion extends at an acute angle with respect thereto. An inner surface of the upper wall, at the juncture of the gum portion and the lip portion, is provided with a groove and the inner surface of the tip portion is provided with another groove. The bottom surfaces of the grooves are aligned with one another, such that a line of sight extends along such surfaces from each end of the blade.

A THIRD EXAMPLE, U.S. Pat. No. 4,114,609 to Moses teaches a laryngoscope blade comprising an essentially straight blade portion have the inner end portion which is curved out of the plane of the straight blade portion, and which curved portion is adapted to be received in the groove defined between the base of the tongue and the epiglottis of a patient whereby the tip end causes the tongue to be moved anteriorly to expose the inlet of the larynx and the straight portion of the blade defines a line of sight directly into the larynx.

A FOURTH EXAMPLE, U.S. Pat. No. 4,592,343 to Upsher teaches an improved laryngoscope having a blade which is curved and tubular and has an improved light means for illuminating the forward end of the blade. In a number of embodiments of the laryngoscope, a light source is mounted in the upper end of the handle of the laryngoscope so the handle can be used with a conventional laryngoscope blade or a non-conventional laryngoscope blade. In one embodiment, the light source is carried by an adapter removably mounted on the handle near the location where the handle and blade are interconnected.

A FIFTH EXAMPLE, U.S. Pat. No. 5,003,962 to Choi teaches a laryngoscope with an improved double-angle blade or spatula which has three segments lengthwise. The first segment extends in a direction substantially normal to the handle to a first bend, at which the blade or spatula is bent toward the handle through an angle of 20 degrees. The second segment extends in a new direction to a second bend inward through an angle of 30 degrees, forming a third segment which extends to the distal tip. A small cylindrical bulb is superposed adjacent to and parallel to the top edge, near the end of the second segment. This is energized by batteries in the handle.

A SIXTH EXAMPLE, U.S. Pat. No. 6,251,069 B1 to Mentzelopoulos et al. teaches a laryngoscope having a flexible blade which is hinged and having in the handle articulation control for the hinged portion of the blade as well as an actuator for a pair of balloons on the blade connected with double-lumen tubes.

It is apparent that numerous innovations for laryngoscopes have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a laryngoscope for simultaneously spreading the epiglottis and the posterior tissue defining the superior opening of the larynx away from each other for opening up the trachea and exposing the larynx that avoids the disadvantages of the prior art.

ANOTHER OBJECT of the present invention is to provide a laryngoscope for simultaneously spreading the epiglottis and the posterior tissue defining the superior opening of the larynx away from each other for opening up the trachea and exposing the larynx that is simple to use.

BRIEFLY STATED, STILL ANOTHER OBJECT of the present invention is to provide an improved laryngoscope of the type having a stationary handle, a stationary blade affixed to the stationary handle, a tip pivotally attached to the stationary blade, a movable handle pivotally attached to the stationary blade, and an arm pivoting the tip downwardly when the movable handle is moved towards the stationary handle depressing the epiglottis. The improvement includes a movable blade pivotally attached to the stationary blade and affixed to the movable handle so as to allow the movable blade to pivot away from the stationary blade when the movable handle is moved towards the stationary handle and spread the posterior tissue defining the superior opening of the larynx away from the epiglottis simultaneously as the tip depresses the epiglottis and both thereby opening up the trachea exposing the larynx, and a lock locking the movable blade in a desired positioned by locking the movable handle affixed thereto.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows:

FIG. 2 is a diagrammatic side elevational view of the laryngoscope of the present invention in use simultaneously spreading the epiglottis and the posterior tissue defining the superior opening of the larynx away from each other for opening up the trachea and exposing the larynx;

FIG. 3 is an enlarged diagrammatic perspective view, with parts broken away, of the area generally enclosed by the dotted curve identified by ARROW 3 in FIG. 2 of the laryngoscope of the present invention in the operative position;

FIG. 4 is an enlarged diagrammatic perspective view, with parts broken away, taken generally in the direction of ARROW 4 in FIG. 3;

FIG. 5 is a reduced diagrammatic perspective view taken generally in the direction of ARROW 5 in FIG. 3 of the laryngoscope of the present invention in the relaxed position;

FIG. 6 is a reduced, exploded diagrammatic perspective view of the area generally enclosed by the dotted curve identified by ARROW 6 in FIG. 3;

FIG. 7 is a diagrammatic perspective view of the area generally enclosed by the dotted curve identified by ARROW 7 in FIG. 3; and FIG. 8 is reduced diagrammatic top plan view taken generally in the direction of ARROW 8 in FIG. 4.

Figure 1:
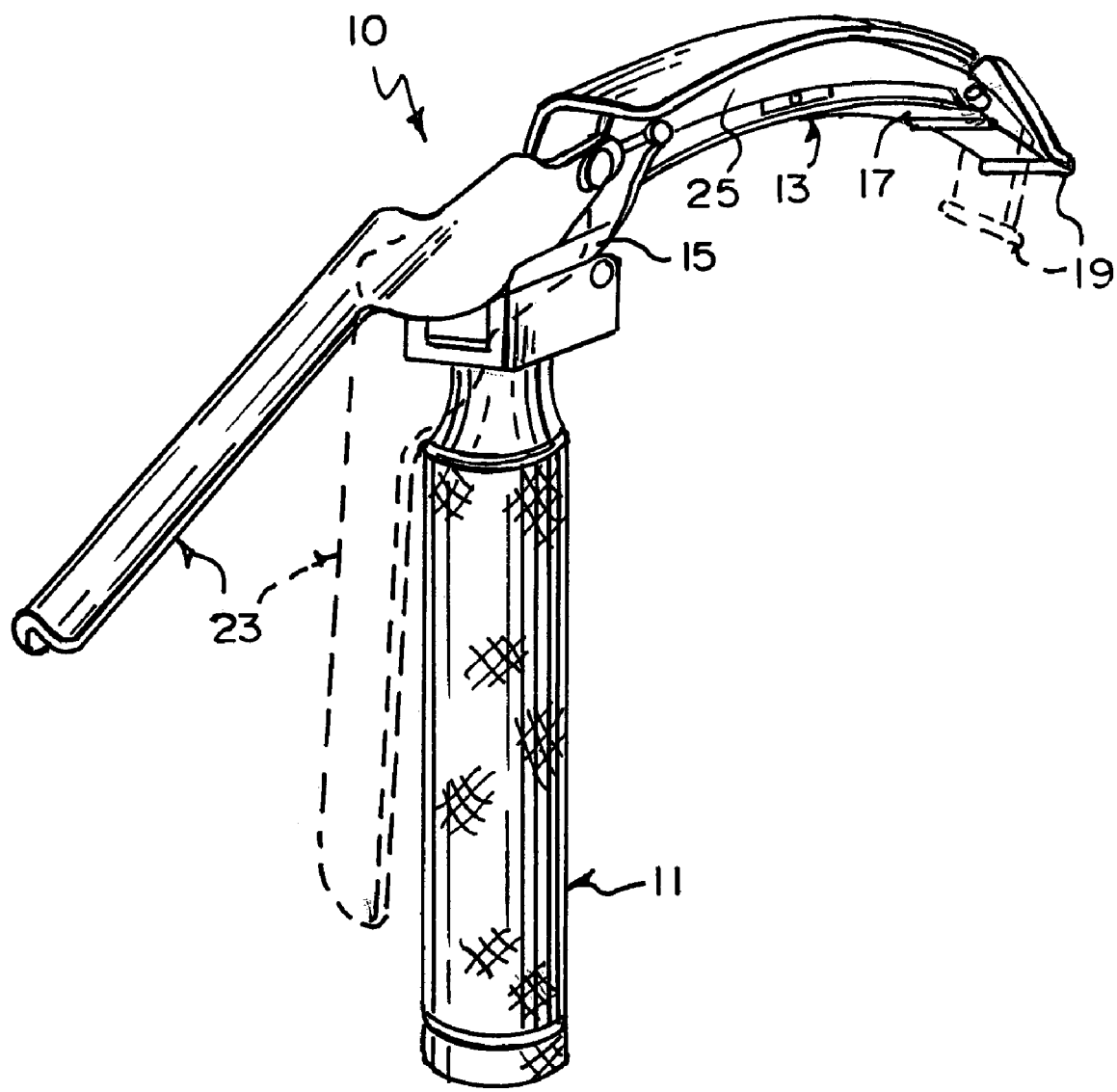
FIG. 1 is a diagrammatic perspective view of a typical prior art laryngoscope.

LIST OF REFERENCE NUMERALS UTILIZED IN THE DRAWING 10 laryngoscope of present invention for simultaneously spreading epiglottis 12 and posterior tissue 14 defining superior opening 16 of larynx 18 away from each other for opening up trachea 20 and exposing larynx 18
11 stationary handle
12 epiglottis
13 stationary blade
14 posterior tissue defining superior opening 16 of larynx 18
15 proximal end of stationary blade 13
16 superior opening of larynx 18
17 distal end of stationary blade 13
18 larynx
19 tip
20 trachea
22 movable blade for spreading posterior tissue 14 defining superior opening 16 of larynx 18 away from epiglottis 12 and opening up trachea 20 exposing larynx 18
23 movable handle
24 lock
25 arm
26 distal end of movable handle 23
28 through bore through distal end 26 of movable handle 23 of lock 24
29 boundary defining through bore 28 through distal end 26 of movable handle 23 of lock 24
30 distal end of stationary handle 11
31 spring end of lock 24
32 strip of lock 24
34 ratchet surface of strip 32 of lock 24
36 proximal end of movable handle 23
38 connector of movable handle 23
40 proximal end of movable blade 22

42 first portion of connector 38 of movable handle 23
44 second portion of connector 38 of movable handle 23
46 fiber optic seeing stylet
48 light tip element of fiber optic seeing stylet 46
50 intubation tube

DETAILED DESCRIPTION OF THE
PREFERRED EMBODIMENT

Referring now to the figures, in which like numerals indicate like parts, and particularly to FIG. 2, the laryngoscope of the present invention is shown generally at 10 for simultaneously spreading the epiglottis 12 and the posterior tissue 14 defining the superior opening 16 of the larynx 18 away from each other for opening up the trachea 20 and exposing the larynx 18.

The configuration of the laryngoscope 10 can best be seen in FIGS. 3–8, and as such, will be discussed with reference thereto.

The laryngoscope 10 comprises a movable blade 22. The movable blade 22 is pivotally attached to the stationary blade 13 and affixed to the movable handle 23 for movement therewith so as to allow the movable blade 22 to pivot away from the stationary blade 13 when the movable handle 23 is moved towards the stationary handle 11 for spreading the posterior tissue 14 defining the superior opening 16 of the larynx 18 away from the epiglottis 12 as the tip 19 depresses the epiglottis 12 and both thereby opening up the trachea 20 exposing the larynx 18.

The laryngoscope further comprises a lock 24. The lock 24 locks the movable blade 22 in a desired position by locking the movable handle 23 affixed thereto.

The lock 24 includes the movable handle 23 having a distal end 26 with a through bore 28 therethrough defined by a boundary 29 and the stationary handle 11 having a distal end 30 from which extends, at a spring end, a strip 32 that passes selectively lockingly through the through bore 28 in the distal end 26 of the movable handle 23 of the lock 24.

The strip 32 of the lock 24 is arcuate and has a ratchet surface 34. The ratchet surface 34 of the strip 32 of the lock 24 selectively engages the boundary 29 of the through bore 28 through the distal end 26 of the movable handle 23.

The movable handle 23 has a proximal end 36 and a connector 38 and the movable blade 22 has a proximal end 40. The connector 38 of the movable handle 23 extends fixedly from the proximal end 36 of the movable handle 23 fixedly to the proximal end 40 of the movable blade 22 so as to allow the movable blade 22 to move with the movable handle 23.

The movable blade 22 extends substantially over the stationary blade 13 plus the tip 19.

The movable blade 22 extends flat and horizontally from the proximal end 40 of the movable blade 22, which is flat and vertical.

The connector 38 of the movable handle 23 is generally L-shaped, and has a first portion 42 and a second portion 44. The first portion 42 of the connector 38 of the movable handle 23 fixedly and coplanarly abuts the proximal end 36 of the movable handle 23. The second portion 44 of the connector 38 of the movable handle 23 extends normally rearwardly from the first portion 42 of the connector 38 of the movable handle 23 and is fixedly attached to the proximal end 40 of the movable blade 22.

It will be understood that each of the elements described above, or two or more together, may also find a useful application in other types of constructions differing from the types described above.

While the invention has been illustrated and described as embodied in a laryngoscope for simultaneously spreading the epiglottis and the posterior tissue defining the superior opening of the larynx away from each other for opening up the trachea and exposing the larynx, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An improved laryngoscope of the type having a stationary handle, a stationary blade having a proximal end from which it extends generally normally forwardly from the stationary handle and a distal end, a tip pivotally attached to the distal end of the stationary blade, a movable handle pivotally attached to the proximal end of the stationary blade and operatively connected to the tip, and an arm operatively attached to the movable handle and the tip and pivoting the tip downwardly when the movable handle is moved towards the stationary handle depressing the epiglottis, said improvement comprising:
   a) movable blade;
   b) said movable blade being pivotally attached to the stationary blade and affixed to the movable handle for movement therewith so as to allow said movable blade to pivot away from the stationary blade when the movable handle is moved towards the stationary handle for spreading the posterior tissue defining the superior opening of the larynx away from the epiglottis simultaneously as the tip depresses the epiglottis and both thereby opening up the trachea exposing the larynx;
   c) a lock:
   d) said lock including the movable handle having a distal end with a through bore therethrough; and
   e) said through bore through the distal end of the movable handle defined by a boundary, wherein said improvement comprises said lock including the stationary handle having a distal end from which extends, at a spring end, a strip.

2. The improved laryngoscope as defined in claim 1, wherein said improvement comprises said lock locking said movable blade in a desired position by locking the movable handle affixed thereto.

3. The improved laryngoscope as defined in claim 1, wherein said improvement comprises said strip of said lock passing selectively lockingly through said through bore in the distal end of the movable handle of said lock.

4. The improved laryngoscope as defined in claim 1, wherein said improvement comprises:
   a) said strip of said lock being arcuate;
   b) said strip of said lock having a ratchet surface; and
   c) said ratchet surface of said strip of said lock selectively engaging said boundary of said through bore through the distal end of the movable handle.

5. The improved laryngoscope as defined in claim 1, wherein said improvement comprises:
   a) the movable handle having a proximal end;
   b) said movable blade having a proximal end; and
   c) the movable handle having a connector.

6. The improved laryngoscope as defined in claim 5, wherein said improvement comprises said connector of the movable handle extending fixedly from said proximal end of the movable handle fixedly to said proximal end of said movable blade so as to allow said movable blade to move with the movable handle.

7. The improved laryngoscope as defined in claim 5, wherein said improvement comprises said movable blade extending flat from said proximal end of said movable blade.

8. The improved laryngoscope as defined in claim 5, wherein said improvement comprises said movable blade extending from said proximal end of said movable blade.

9. The improved laryngoscope as defined in claim 5, wherein said improvement comprises said proximal end of said movable blade being flat.

10. The improved laryngoscope as defined in claim 5, wherein said improvement comprises said connector of the movable handle being generally L-shaped.

11. The improved laryngoscope as defined in claim 5, wherein said improvement comprises said connector of the movable handle having:
   a) a first portion; and
   b) a second portion.

12. The improved laryngoscope as defined in claim 11, wherein said improvement comprises said first portion of said connector of the movable handle fixedly and coplanarly abutting said proximal end of the movable handle.

13. The improved laryngoscope as defined in claim 12, wherein said improvement comprises said second portion of said connector of the movable handle extending normally from said first portion of said connector of the movable handle.

14. The improved laryngoscope as defined in claim 12, wherein said improvement comprises said second portion of said connector of the movable handle being fixedly attached to said proximal end of said movable blade.

15. The improved laryngoscope as defined in claim 1, wherein said improvement comprises said movable blade extending substantially over the stationary blade plus the tip.

16. An improved laryngoscope of the type having a stationary handle, a stationary blade having a proximal end from which it extends generally normally outwardly from the stationary handle and a distal end, a tip pivotally attached to the distal end of the stationary blade, a movable handle pivotally attached to the proximal end of the stationary blade and operatively connected to the tip, and an arm operatively attached to the movable handle and the tip and pivoting the tip downwardly when the movable handle is moved towards the stationary handle depressing the epiglottis, said improvement comprising:
   a) a movable blade;
   b) said movable blade being pivotally attached to the stationary blade and affixed to the movable handle for movement therewith so as to allow said movable blade to pivot away from the stationary blade when the movable handle is moved towards the stationary handle for spreading the posterior tissue defining the superior opening of the larynx away from the epiglottis simultaneously as the tip depresses the epiglottis and both thereby opening up the trachea exposing the larynx;
   c) a lock;
   d) said lock locking said movable blade in a desired position by locking the movable handle affixed thereto;
   e) said lock including the movable handle having a distal end with a through bore therethrough;
   f) said through bore through the distal end of the movable handle defined by a boundary;
   g) said lock including the stationary handle having a distal end from which extends, at a spring end, a strip;
   h) said strip of said lock passing selectively lockingly through said through bore in the distal end of the movable handle of said lock;
   i) said strip being arcuate;
   j) said strip of said lock having a ratchet surface;
   k) said ratchet surface of said strip of said lock selectively engaging said boundary of said through bore through the distal end of the movable handle;
   l) the movable handle having a proximal end;
   m) said movable blade having a proximal end;
   n) the movable handle having a connector;
   o) said connector of the movable handle extending fixedly from said proximal end of the movable handle fixedly to said proximal end of said movable blade so as to allow said movable blade to move with the movable handle;
   p) said movable blade extending substantially over the stationary blade plus the tip;
   q) said movable blade extending flat from said proximal end of said movable blade;
   r) said movable blade extending from said proximal end of said movable blade;
   s) said proximal end of said movable blade being flat;
   t) said connector of the movable handle being generally L-shaped;
   u) said connector of the movable handle having:
      i) a first portion; and
      ii) a second portion;
   v) said first portion of said connector of the movable handle fixedly and coplanarly abutting said proximal end of the movable handle;
   w) said second portion of said connector of the movable handle extending normally from said first portion of said connector of the movable handle; and
   x) said second portion of said connector of the movable handle being fixedly attached to said proximal end of said movable blade.

* * * * *